United States Patent
An et al.

(10) Patent No.: US 10,675,472 B2
(45) Date of Patent: *Jun. 9, 2020

(54) MULTI-SITE PACING CAPTURE VERIFICATION

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Yinghong Yu, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/884,417

(22) Filed: Oct. 15, 2015

(65) Prior Publication Data

US 2016/0106987 A1    Apr. 21, 2016

Related U.S. Application Data

(60) Provisional application No. 62/065,108, filed on Oct. 17, 2014.

(51) Int. Cl.
*A61N 1/37* (2006.01)
*A61N 1/368* (2006.01)
(Continued)

(52) U.S. Cl.
CPC .......... *A61N 1/371* (2013.01); *A61B 5/0452* (2013.01); *A61N 1/3684* (2013.01); *A61N 1/36578* (2013.01)

(58) Field of Classification Search
CPC .......... A61N 1/3622; A61N 1/3627; A61N 1/36578; A61N 1/368; A61N 1/3684; A61N 1/371; A61N 1/3712; A61B 5/7246
See application file for complete search history.

(56) References Cited

U.S. PATENT DOCUMENTS 4,763,646 A * 8/1988 Lekholm ............ A61N 1/36514
607/14
6,772,008 B2    8/2004 Zhu et al.
(Continued)

FOREIGN PATENT DOCUMENTS

| CN | 107072577 A | 8/2017 |
| WO | WO-2012087760 A1 | 6/2012 |
| WO | WO-2016061366 A1 | 4/2016 |

OTHER PUBLICATIONS

Asbach, Stefan, et al., "Vector Selection of a Quadripolar Left Ventricular Pacing Lead Affects Acute Hemodynamic Response to Cardiac Resynchronization Therapy: A Randomized Cross-Over Trial", Plos One; vol. 8; Issue 6, (Jun. 2013), 1-6.

(Continued)

*Primary Examiner* — Eugene T Wu
(74) *Attorney, Agent, or Firm* — Schwegman Lundberg & Woessner, P.A.

(57) ABSTRACT

Systems and methods for evaluating electrostimulation of a heart are disclosed. A system can comprise an electrostimulation circuit that can deliver multi-site electrostimulation, including pacing at two or more sites of the heart during the same cardiac cycle. The system can comprise a heart sound sensor circuit configured to sense a heart sound (HS) signal during multi-site stimulation. The heart sound sensor circuit can also sense HS signals in response to uni-site stimulation at a specified site capturing at least a portion of the heart. The system can comprise a pacing analyzer circuit that uses the HS signals during the multi-site stimulation and during the uni-site stimulation to determine a capture status indication that indicates whether the multi-site stimulation captures the two or more sites of the heart, and can be one of a full capture indication, a partial capture indication, or a loss of capture indication.

20 Claims, 7 Drawing Sheets

(51) Int. Cl.
*A61B 5/0452* (2006.01)
*A61N 1/365* (2006.01)

(56) References Cited

U.S. PATENT DOCUMENTS

| | | | |
|---|---|---|---|
| 7,392,085 B2 | 6/2008 | Warren et al. | |
| 7,620,452 B1 | 11/2009 | Russie | |
| 7,853,327 B2* | 12/2010 | Patangay | A61B 7/04 600/513 |
| 8,055,343 B2 | 11/2011 | Gandhi et al. | |
| 8,509,890 B2 | 8/2013 | Keel et al. | |
| 8,527,049 B2 | 9/2013 | Koh et al. | |
| 8,666,490 B1* | 3/2014 | Ryu | A61N 1/3712 607/28 |
| 8,886,313 B2 | 11/2014 | Siejko et al. | |
| 8,972,228 B2 | 3/2015 | Ghosh et al. | |
| 2003/0083710 A1* | 5/2003 | Ternes | A61N 1/3712 607/27 |
| 2003/0083711 A1* | 5/2003 | Yonce | A61B 5/04525 607/27 |
| 2005/0137638 A1* | 6/2005 | Yonce | A61N 1/3712 607/28 |
| 2009/0030334 A1* | 1/2009 | Anderson | A61N 1/3702 600/528 |
| 2009/0043351 A1 | 2/2009 | Sathaye et al. | |
| 2010/0042174 A1 | 2/2010 | Koh et al. | |
| 2012/0078320 A1 | 3/2012 | Schotzko et al. | |
| 2012/0101546 A1 | 4/2012 | Stadler et al. | |
| 2012/0191154 A1 | 7/2012 | Ryu et al. | |
| 2013/0030484 A1* | 1/2013 | Zhang | A61N 1/37264 607/17 |
| 2013/0184777 A1 | 7/2013 | Hellman et al. | |
| 2013/0289640 A1 | 10/2013 | Zhang et al. | |
| 2013/0289641 A1 | 10/2013 | Gustafsson et al. | |
| 2013/0296962 A1 | 11/2013 | Keel et al. | |
| 2014/0277243 A1* | 9/2014 | Maskara | A61N 1/371 607/28 |
| 2015/0165204 A1 | 6/2015 | Yu et al. | |
| 2015/0165212 A1 | 6/2015 | Saha et al. | |
| 2016/0206887 A1* | 7/2016 | Maskara | A61N 1/371 |
| 2017/0001011 A1 | 1/2017 | An et al. | |

OTHER PUBLICATIONS

Pappone, Carlo, et al., "Cardiac Resynchronization Therapy with Multisite Left Ventricular Pacing Improves Acute Hemodynamic Response in Patients", Abstract 13412; 2012 AHA, (2012), 1-2.

"International Application Serial No. PCT/US2015/055762, International Search Report dated Jan. 12, 2016", 6 pgs.

"International Application Serial No. PCT/US2015/055762, Written Opinion dated Jan. 12, 2016", 7 pgs.

"International Application Serial No. PCT/US2015/055762, International Preliminary Report on Patentability dated Apr. 27, 2017", 9 pgs.

"U.S. Appl. No. 15/187,252, Non Final Office Action dated Sep. 28, 2017", 8 pgs.

* cited by examiner

US 10,675,472 B2

MULTI-SITE PACING CAPTURE VERIFICATION

CLAIM OF PRIORITY

This application claims the benefit of priority under 35 U.S.C. § 119(e) of U.S. Provisional Patent Application Ser. No. 62/065,108, filed on Oct. 17, 2014, which is herein incorporated by reference in its entirety.

TECHNICAL FIELD

This document relates generally to medical devices, and more particularly, to devices and methods for stimulating excitable tissue and evaluating resultant physiologic response.

BACKGROUND

Congestive heart failure (CHF) is a leading cause of death in the United States affecting approximately 670,000 individuals. CHF occurs when the heart is unable to adequately supply enough blood to maintain a healthy physiological state. CHF can be treated by drug therapy, or by an implantable medical device (IMD) such as for providing cardiac pacing therapies, including resynchronization therapy (CRT) to correct cardiac dyssynchrony within a ventricle or between ventricles.

The IMD can chronically stimulate excitable tissues or organs, such as a heart, to treat abnormal cardiac rhythms or to help improve cardiac performance in a patient with CHF. Such ambulatory medical devices can have at least first and second electrodes that can be positioned within the heart or on a surface of the heart for contacting the cardiac tissue. The electrodes can be electrically coupled to an electronics unit such as a pulse generator, such as via a lead, and can be used to deliver one or more electrostimulations to the heart, such as to restore or to improve the normal heart function.

Overview

Cardiac stimulation using an implantable medical device (IMD) can involve one or more implantable leads that can be transvascularly inserted into one of the heart chambers, such as an atrium or a ventricle. Stimulation of the heart can be accomplished through direct myocardium stimulation using at least first and second electrodes that can be electrically connected to the IMD and in close contact with the cardiac tissue. The electrodes can be positioned along the one or more implantable leads. The stimulation can be provided at specified stimulation strength (e.g., stimulation energy) sufficient to capture the heart tissue, that is, the stimulation can effectively cause depolarization propagating to a part or the entirety of the heart.

To assure effective cardiac stimulation, evoked electrical depolarization or mechanical contraction can be sensed to evaluate the capture status. In some cases, a loss of capture can occur when the stimulation is ineffective in causing propagated depolarization of the heart tissue. In some other cases, a capture can occur with an abnormally high stimulation threshold. A stimulation threshold represents minimum amount of electrical energy required to initiate cardiac depolarization, and thereby causing capture. An elevated stimulation threshold relates to more significant power drain to achieve and maintain desired cardiac stimulation therapy. The loss of capture or the elevated stimulation threshold can be caused by various reasons, including improper stimulation configuration (e.g., pacing output and pacing vector selection), reduced excitability of the tissue at the stimulation site (such as myocardial infarction), lead dislodgement, maturation, or failure, or poor connection of the electrostimulation system.

During CRT therapy, synchronized stimulation can be applied to the left ventricle (LV) and the right ventricle (RV) of a heart. Effective capture is required during the pacing of the LV and RV. Stimulation of multiple sites on the heart, such as multi-site LV pacing, has also be proposed as a CHF therapy aiming to improve the cardiac hemodynamic outcome in CHF patients. Such multi-site stimulation can involve electrostimulation delivered at two or more sites of the heart within a cardiac cycle, such as simultaneous stimulation or separated by a specified temporal offset less than a sensed or paced time interval value of the cardiac cycle. Like other modes of cardiac pacing, multi-site stimulation also requires timely recognition of capture status, so as to achieve effective cardiac pacing without excessive energy consumption. However, because of the stimulation at multiple sites are within the same cardiac cycle, the resulting evoked response can be different than that obtained during uni-site stimulation where electrostimulation is applied only at one site. The present inventors have recognized, among other things, substantial challenges and a demand for improved systems and methods for recognizing capture status during multi-site stimulation.

This document discusses, among other things, a system for evaluating electrostimulation of a heart. The system can comprise an electrostimulation circuit that can deliver multi-site electrostimulation, including pacing at two or more sites of the heart within the same cardiac cycle. A heart sound sensor circuit can sense a heart sound (HS) signal during multi-site stimulation. The heart sound sensor circuit can also sense HS signals in response to uni-site stimulation at a specified site capturing at least a portion of the heart. The system can also comprise a pacing analyzer circuit that can compute a similarity metric between the HS signal during multi-site stimulation and the HS signal during uni-site stimulation, and determine a capture status indication indicating whether the multi-site stimulation captures the two or more sites of the heart.

In Example 1, a system can comprise an electrostimulation circuit, a heart sound (HS) sensor circuit, and a pacing analyzer circuit. The electrostimulation circuit can deliver electrostimulation to two or more sites of the heart, such as two or more sites in a chamber of the heart, within a cardiac cycle. The HS sensor circuit can sense a HS signal during the delivery of the electrostimulation to the two or more sites. The pacing analyzer circuit, in communication with the HS sensor circuit, can determine a capture status indication using the sensed HS signal. The capture status indication indicates whether the electrostimulation captures at least the two or more sites in the chamber, and can include one or more of a full capture indication, a partial capture indication, or a loss of capture indication. The full capture indication can indicate that each of the two or more sites is captured by the electrostimulation. The partial capture indication can indicate that at least one of the two or more sites is captured by the electrostimulation, and at least another one of the two or more sites is not captured by the electrostimulation. The loss of capture indication can indicate none of the two or more sites is captured by the electrostimulation.

In Example 2, the electrostimulation circuit of Example 1 can deliver a first electrostimulation to a first site during a first cardiac cycle, deliver a second electrostimulation to a second site during a second cardiac cycle, and deliver a third electrostimulation to both the first and second sites during a third cardiac cycle, simultaneously or separated by separated by a specified temporal offset that is less than a sensed or paced time interval value of the third cardiac cycle. The HS sensor circuit can sense a first HS signal in response to the first electrostimulation captures at least a portion of the heart, sense a second HS signal in response to the second electrostimulation captures at least a portion of the heart, and sense a third HS signal during the delivery of the third electrostimulation. The pacing analyzer circuit can determine the capture status indication using a comparison between the third HS signal and at least one of the first or second HS signals. The capture status indication indicates whether the third electrostimulation captures both the first and second sites.

In Example 3, the pacing analyzer circuit of Example 2 can generate a third HS feature vector using the third HS signal, and at least one of first or second HS feature vector using respectively the first or second HS signal, where the first, second, or third feature vector each can include a respective morphological or statistical feature. The pacing analyzer circuit can compute a dissimilarity metric between the third HS feature vector and at least one of the first or second feature vector, and determine the capture status indication in response to the dissimilarity metric meeting a specified criterion.

In Example 4, the pacing analyzer circuit of Example 3 can compute a first dissimilarity metric between the third HS feature vector and the first HS feature vector, and a second dissimilarity metric between the third HS feature vector and the second HS feature vector. The pacing analyzer circuit can determine a full capture indication in response to the first and second dissimilarity metrics falling below respective thresholds, or a partial capture indication in response to one of the first and second dissimilarity metrics exceeding the respective threshold, or a loss of capture indication in response to the first and second dissimilarity metrics exceeding the respective thresholds.

In Example 5, the third HS feature vector of any one of Examples 3 or 4 can include a portion of the third HS signal. The first or second HS feature vector can include respectively a portion of the first or second HS signal including the specified HS component. The specified HS component can include a specified HS component such as one or more of S1, S2, S3 or S4 heart sound components.

In Example 6, the third HS feature vector of any one of Examples 3 or 4 can include an intensity parameter of the third HS signal. The first or second HS feature vector can include respectively an intensity parameter of the first or second HS signal. The intensity parameter can include amplitude of one or more of S1, S2, S3 or S4 heart sound components.

In Example 7, the third HS feature vector of any one of Examples 3 or 4, wherein the third HS feature vector can include a cardiac timing interval (CTI) parameter computed using the third HS signal, and the first or second HS feature vector can include respectively the CTI parameter computed using the first or second HS signal. The CTI parameter can include one or more of a systolic time interval, a pre-ejection interval, a diastolic interval, or a left ventricle ejection time.

In Example 8, the dissimilarity metric of any one of Examples 3 through 7 can include a distance between the third HS feature vector and at least one of the first or second HS feature vector in a vector space.

In Example 9, the pacing analyzer circuit of any one of Example 3 through 8 can compute an ensemble average of a portion of the third HS signal over multiple physiological cycles, and an ensemble average of a portion of the at least one of the first or second HS signal over multiple physiological cycles. The dissimilarity metric can include a distance between the ensemble average of the portion of the third HS signal and the ensemble average of the portion of the at least one of the first or second HS signal.

In Example 10, the pacing analyzer circuit of any one of Examples 3 through 9 can compute a transformation of a portion of third HS signal, and a transformation of a portion of the at least one of the first or second HS signal. The dissimilarity metric can include a distance between the transformation of the portion of third HS signal and the transformation of the portion of the at least one of the first or second HS signal.

In Example 11, the transformation of Example 10 can include a projection of a signal onto a subspace or a specified direction in the vector space.

In Example 12, the system of any one of Examples 1 through 11 further can comprise a therapy controller circuit coupled to the electrostimulation circuit. The therapy controller circuit can determine at least one therapy parameter based on the capture status indication. The electrostimulation circuit can deliver the electrostimulation according to the determined therapy parameter.

In Example 13, the HS sensor circuit of any one of Examples 1 through 12 can be coupled to an accelerometer or an acoustic sensor configured to detect mechanical or acoustic activity of the heart indicative of HS.

In Example 14, the electrostimulation circuit of any one of Examples 1 through 13 can deliver electrostimulation to two or more sites of the left ventricle (LV) within the same cardiac cycle.

In Example 15, the electrostimulation circuit of Example 14 can stimulate the two or more sites of the LV via two or more electrodes removably positioned on the two or more sites of the LV.

In Example 16, a method for evaluating electrostimulation of a heart can comprise receiving first and second heart sound (HS) signals. The first HS signal is obtained in response to electrostimulation to a first site of the heart during a first cardiac cycle capturing at least a portion of the heart, the second HS signal is obtained in response to electrostimulation to a different second site of the heart during a second cardiac cycle capturing at least a portion of the heart. The method can also include delivering electrostimulation to two or more sites during a third cardiac cycle, simultaneously or separated by a specified temporal offset that is less than a sensed or paced time interval value of the third cardiac cycle, and sensing a third HS signal during the delivery of the electrostimulation to the two or more sites of the heart. The two or more sites can include the first and second sites of the heart. The method can include determining a capture status indication using the third HS signal and at least one of the first or second HS signals. The capture status indication can indicate whether the electrostimulation of the two or more sites captures at least a portion of the heart. The capture status indication can include one or more of a full capture indication, a partial capture indication, or a loss of capture indication. The full capture indication can indicate that each of the two or more sites is captured by the electrostimulation. The partial capture indication can indicate that at least one of the two or more sites is captured by the electrostimulation, and at least another one of the two or more sites is not captured by the electrostimulation. The loss of capture indication can indicate none of the two or more sites is captured by the electrostimulation.

In Example 17, the first and second HS signals of Example 16 can be received during stimulation of respective first and second sites of a left ventricle (LV) of the heart.

In Example 18, the method of Example 16 further can comprise generating a third HS feature vector using the third HS signal, and generating at least one of first or second HS feature vector using respectively the first or second HS signal. The first, second, or third feature vector each can include a respective morphological or statistical feature. The method further can comprise computing a dissimilarity metric between the third HS feature vector and at least one of the first or second feature vector, and determining the capture status indication in response to the dissimilarity metric meeting a specified criterion.

In Example 19, the dissimilarity metric of Example 18 can include a first dissimilarity metric between the third HS feature vector and the first HS feature vector, and a second dissimilarity metric between the third HS feature vector and the second HS feature vector. The determining the capture status indication can include determining a full capture indication in response to the first and second dissimilarity metrics falling below respective thresholds, or a partial capture indication in response to one of the first and second dissimilarity metrics exceeding the respective threshold, or a loss of capture indication in response to the first and second dissimilarity metrics exceeding the respective thresholds.

In Example 20, the dissimilarity metric of Example 18 can include a distance between the third HS feature vector and at least one of the first or second HS feature vector in a vector space.

In Example 21, the first, second, or third HS feature vector of Example 18 each can include one or more of a signal portion, a transformation of a signal portion, an intensity measure, or a cardiac timing interval parameter of the respective HS signals.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for stimulating excitable tissue such as a heart and evaluating physiologic responses to the stimulation. The stimulation, such as an electrostimulation sequence, can be applied to multiple sites of the heart such as multi-sites of the left ventricle (LV) of the heart, to restore or improve cardiac performance. The physiologic response to the cardiac electrostimulation, such as sensed by a heart sound sensor, can be analyzed to produce a capture status indication indicating whether the electrostimulation at all the stimulation sites capture the cardiac tissue, or only the electrostimulation at a part of the stimulation sites capture the cardiac tissue. The capture status indication can be used to adjust pacing therapy such as to optimize configuration of the multi-site cardiac stimulation.

Figure 1:
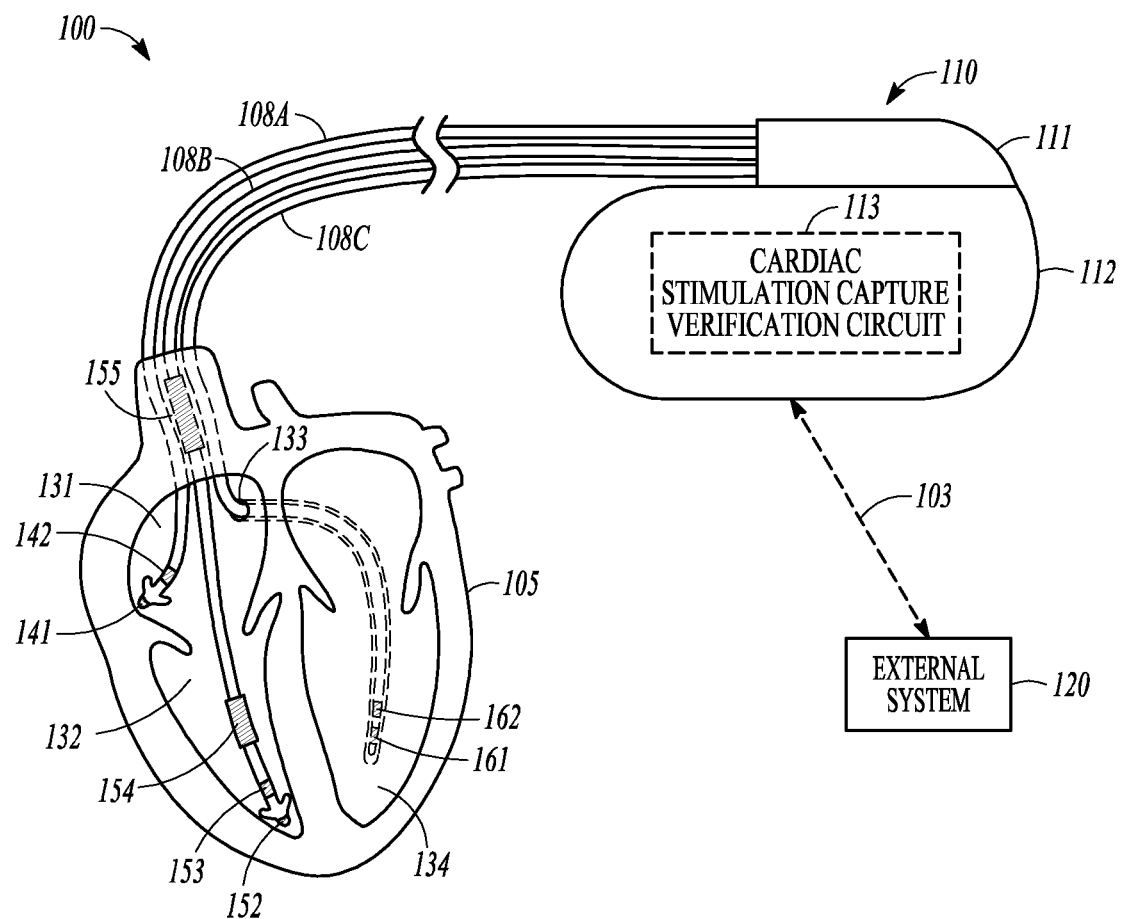
FIG. 1 illustrates an example of a Cardiac Rhythm Management (CRM) system and portions of an environment in which the CRM system can operate.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV. Additional electrodes can be included in or along the lead 108C. In some examples (not shown in FIG. 1), at least one of the leads 108A-C, or an additional lead other than the leads 108A-C, can be implanted under the skin surface without being within a heart chamber, or at or close to heart tissue.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a cardiac stimulation capture verification circuit 113. The cardiac stimulation capture verification circuit 113 can be configured to detect physiologic responses to electrostimulation at two or more sites of the heart 105, such as multi-site pacing of two or more sites in the left ventricle (LV) 134 such as via electrodes 161 and 162. The physiologic response can include a heart sound (HS) signal such as sensed by a physiologic sensor communicatively coupled to the CRM system 100. The cardiac stimulation capture verification circuit 113 can use the sensed HS signal to determine a capture status indication as one of a full capture indication, a partial capture indication, or a loss of capture indication. The capture status indication can indicate whether the electrostimulation captures at least the two or more sites. Examples of the cardiac stimulation capture verification circuit 113 are described below, such as with reference to FIGS. 2-5.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The cardiac stimulation capture verification circuit 113 can be implemented at the external system 120 such as using data extracted from the IMD 110 or data stored in a memory within the external system 120. Portions of the cardiac stimulation capture verification circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
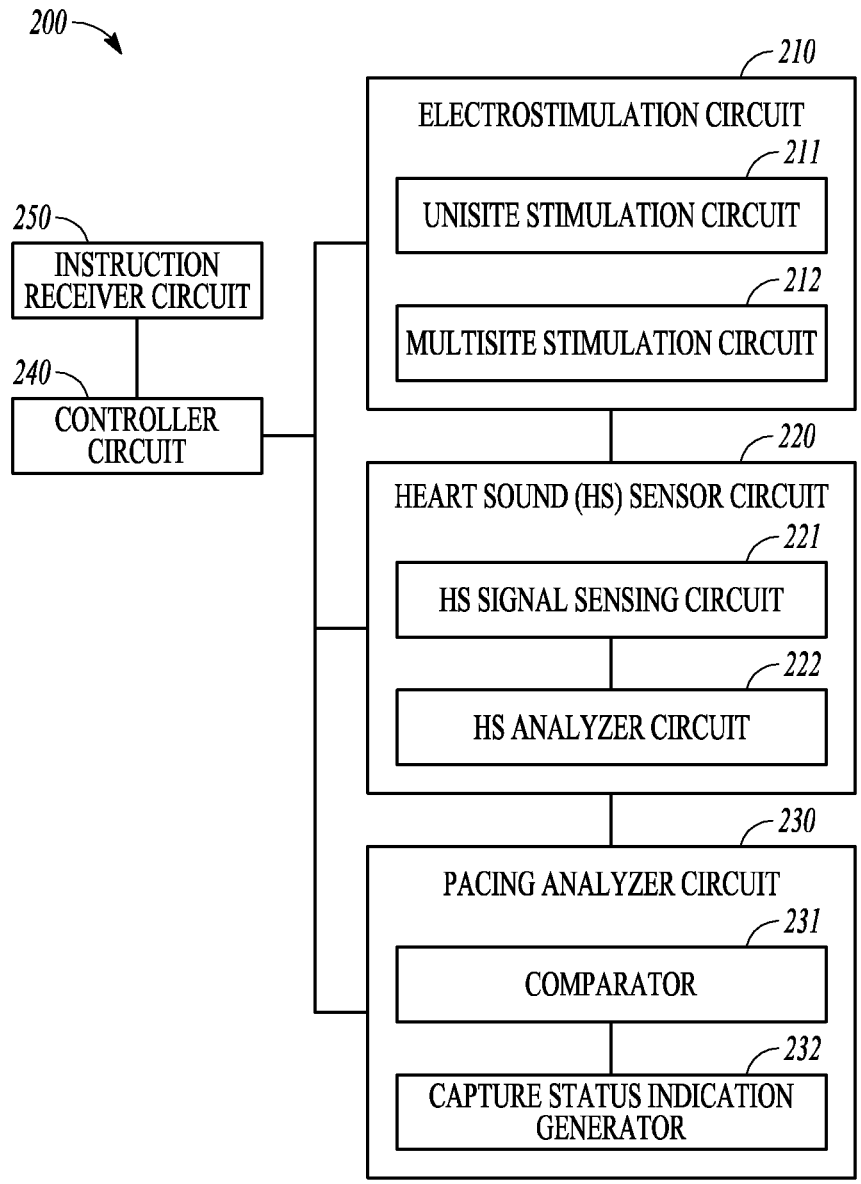
FIG. 2 illustrates an example of a heart sound (HS) based multi-site pacing capture verification circuit.

FIG. 2 illustrates an example of a heart sound (HS) based multi-site pacing capture verification circuit 200, which can be an embodiment of the cardiac stimulation capture verification circuit 113. The HS based multi-site pacing capture verification circuit 200 can include one or more of an electrostimulation circuit 210, a heart sound (HS) sensor circuit 220, a pacing analyzer circuit 230, a controller circuit 240, and an instruction receiver circuit 250.

The electrostimulation circuit 210 can be configured to deliver electrostimulation to two or more sites of a heart, such as two or more sites of a chamber of the heart. The electrostimulation, such as a pulse train, can be produced by the IMD 100 or an external pulse generator, and delivered to the two or more sites of the heart via a pacing delivery system such as one or more of the leads 108A-C and the respectively attached electrodes. The electrostimulation can be delivered between an anode and a cathode. The anode and the cathode form a pacing vector. The electrostimulation can include a unipolar or a bipolar pacing configuration. The unipolar pacing can involve stimulation between an electrode positioned at or near a target stimulation site of the heart and a return electrode such as the IMD can 112. The bipolar pacing can involve stimulation between two electrodes on one or more of the leads 108A-C.

As illustrated, the electrostimulation circuit 210 can include a uni-site stimulation circuit 211 and a multi-site stimulation circuit 212. The uni-site stimulation circuit 211 can be configured to deliver uni-site electrostimulation that involves stimulating one specified site of the heart. In an example, the uni-site stimulation circuit 211 can deliver a first electrostimulation to a first site during a first cardiac cycle, and a second electrostimulation to a second site during a second cardiac cycle. The multi-site stimulation circuit 212 can be configured to deliver stimulation to two or more sites of the heart within the same cardiac cycle. In an example, the multi-site stimulation circuit 212 can deliver a third electrostimulation to both the first and second sites of the heart within a third cardiac cycle, simultaneously or separated by a specified temporal offset less than a sensed or paced time interval value of the cardiac cycle. An example of the temporal offset is approximately between 0-100 msec.

The two or more sites for electrostimulation can include anatomical regions inside, or on an epicardial surface of, one or more heart chambers, including right atrium (RA), right ventricle (RV), left atrium (LA), and left ventricle (LV), or tissues surrounding any of the chambers. In an example, the multi-site stimulation circuit 212 can deliver electrostimulation to at least a site at RV and a site at LV. In another example, the multi-site stimulation circuit 212 can deliver electrostimulation to two or more sites at the same chamber, such as two or more sites in LV which is hereinafter referred to as "multi-site LV pacing." The multi-site LV pacing can be achieved using two or more LV pacing vectors. For each LV pacing vector, at least one of the anode or the cathode can be selected from the two or more electrodes on the LV lead 133 (such as electrodes 161 and 162). In an example, the electrostimulation circuit 210 can deliver multi-site LV pacing using one or more of a bipolar pacing between two LV electrodes, a bipolar pacing between an LV electrode and a RV or RA electrode, a tripolar pacing between one or more LV electrodes and a RV or RA electrode, or a unipolar pacing between an LV electrode and the IMD can 112. The electrostimulation can be delivered to the two or more sites within a cardiac cycle, such as simultaneous stimulation or separated by a specified temporal offset less than a sensed or paced time interval value of the cardiac cycle. An example of the temporal offset is approximately between 0-100 milliseconds (msec).

The heart sound (HS) sensor circuit 220 can include a HS signal sensing circuit 221 and a HS analyzer circuit 222. The HS signal sensing circuit 221 can sense a physiologic response during the stimulation of the two or more sites of the heart, such as two or more sites in a chamber of the heart. The HS signal sensing circuit 221 can be coupled to a HS sensor configured to detect a HS signal indicative of mechanical or vibrational activities of the heart. In an example, the HS sensor can include an accelerometer configured to sense an acceleration signal indicative of the heart sound of the subject. In another example, the HS sensor can include an acoustic sensor configured to sense an acoustic energy indicative of the heart sound of the subject. Other examples of HS sensors can include microphone, piezo-based sensor, or other vibrational or acoustic sensors.

The HS sensor can be an implantable, wearable, or otherwise ambulatory sensor, and placed external to the patient or implanted inside the body. In an example, the HS sensor can be included in at least one part of an implantable system, such as the IMD 110, or one of the leads 108A-C coupled to the IMD 110. Alternatively or additionally, the HS sensing circuit 221 can receive a HS signal from a device capable of collecting or storing HS information. Examples of such a device can include an external programmer, an electronic medical record system, a memory unit, or other data storage devices.

The HS analyzer circuit 222 can process the sensed HS signal, including amplification, digitization, filtering, or other signal conditioning operations. In an example, the HS analyzer circuit 222 can include one or more signal filters that can filter the sensed HS signal to a specified frequency range. For example, the HS analyzer circuit 222 can include a bandpass filter adapted to filter the HS signal to a frequency range of approximately between 5 and 90 Hz. In another example, the HS analyzer circuit 222 can include a bandpass filter adapted to filter the HS signal to a frequency range of approximately between 9 and 90 Hz. In an example, the HS analyzer circuit 222 can include a double or higher-order differentiator configured to calculate a double or higher-order differentiation of the sensed heart sound signal.

The HS analyzer circuit 222 can detect, using the processed HS signal, one or more HS components, including S1, S2, S3 or S4 heart sounds. In an example, the HS analyzer circuit 222 can generate respective time windows for detecting the one or more HS components. The time windows can be determined with reference to a physiologic event such as a Q wave, an R wave, or a QRS complex from a surface electrocardiograph (ECG), a subcutaneous ECG, or a cardiac sensing or pacing event in an intracardiac electrogram (EGM). For example, an S1 detection window can begin at 50 milliseconds (msec) following an R wave and have a duration of 300 msec. An S2 detection window can begin at specified offset following a detected R wave or S1 heart sound. An S3 detection window can be determined using at least one cardiac signal feature such as the R-wave timing or the timing of S2 heart sound. The S3 detection window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate.

The HS analyzer circuit 222 can detect an HS component within the respective HS detection window based on signal amplitude or energy. For example, HS signal energy within a S2 detection window can be computed and compared to a S2 energy threshold, and an S2 component is detected in response to the HS signal energy exceeds the S2 energy threshold. In an example, the HS analyzer circuit 222 can detect an HS component adaptively by tracking the temporal locations of the previously detected HS features. For example, an S3 heart sound can be detected by adaptively tracking the timing of historically detected S3 heart sounds. A dynamic programming algorithm can be used to detect and track the S3 heart sound within the S3 detection window, such as that disclosed in the commonly assigned Patangay et al. U.S. Pat. No. 7,853,327 entitled "HEART SOUND TRACKING SYSTEM AND METHOD," which is hereby incorporated by reference in its entirety.

The HS analyzer circuit 222 can generate one or more HS features using the detected HS component. The HS features can include morphological features or statistical features. The morphological features can include maximum or minimum within a specified period, amount of change within a specified period, positive or negative slope that indicates the rate of increase or rate of decrease, signal power spectral density at a specified frequency range, among other morphological descriptors. The statistical features can include mean, median, or other central tendency measures, standard deviation, variance, correlation, covariance, other higher-order statistics computed from a plurality of HS measurements, among others. The statistical features can also include parameters derived from a statistical distribution of the plurality of HS measurements. Examples of the HS analyzer circuit 222 are discussed below, such as with reference to FIG. 3.

The pacing analyzer circuit 230, in communication with the HS sensor circuit 220, can be configured to determine capture status using the one or more HS features. The pacing analyzer circuit 230 can include a comparator 231, and a capture status indication generator 232. The comparator 231 can compare the HS features obtained during various electrostimulation configurations. In an example, the comparator 231 can compare the HS features during uni-site stimulation (such as uni-site LV pacing), and the HS features during multi-site stimulation (such as multi-site LV pacing). Based on the comparison, the capture status indication generator 232 can then determine a capture status indication. The capture status indication can indicate whether the electrostimulation at all the stimulation sites capture the cardiac tissue, or only the electrostimulation at a part of the stimulation sites capture the cardiac tissue. In some examples, the capture status indication, along with other device information, can be displayed to a system user. In some examples, the electrostimulation circuit 210 can program multi-site stimulation based at least on the capture status indication, such as by adjusting one or more stimulation intensity parameters (e.g., amplitude, pulse width, duty cycle, or frequency), adjusting stimulation sites, adjusting stimulation modes or configuration of stimulation vectors, among others. Examples of the determining the capture status indication based on the HS features are discussed below, such as with reference to FIG. 4.

The controller circuit 240 can receive external programming input from the instruction receiver circuit 250 to control the operations of the electrostimulation circuit 210, the HS sensor circuit 220, the pacing analyzer circuit 230, and the data flow and instructions between these components and respective subcomponents. Examples of the instructions received by instruction receiver 240 can include parameters for delivering electrostimulation (including pacing configurations and stimulation frequency and energy), sensing HS, generating HS features, and determining the capture status based on the HS features. The instruction receiver circuit 250 can include a user interface configured to present programming options to a system user, and receive the system user's programming input. In an example, at least a portion of the instruction receiver circuit 250, such as the user interface, can be implemented in the external system 120.

Figure 3:
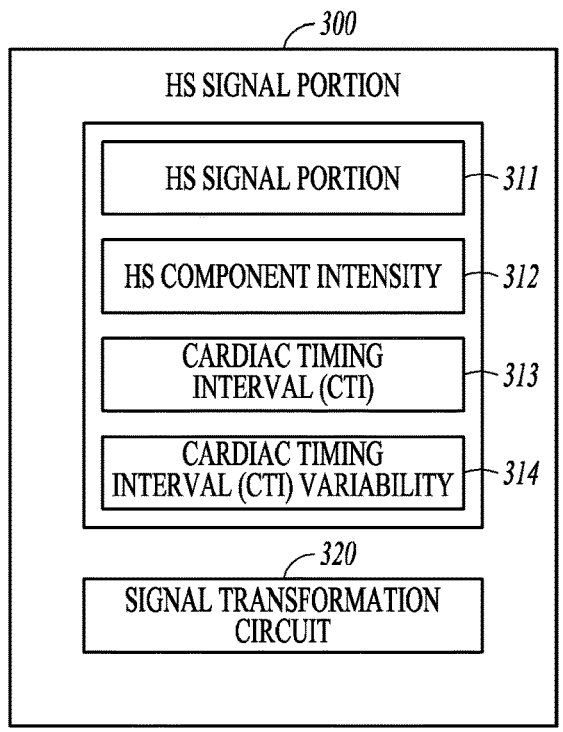
FIG. 3 illustrates an example of a HS feature generator circuit.

FIG. 3 illustrates an example of a heart sound (HS) feature generator circuit 300, which can be an embodiment of the HS analyzer circuit 222. The feature generator circuit 300 can generate, from the sensed HS signal or the HS components (e.g., S1, S2, S3 or S4 heart sound), one or more morphological or statistical HS features. As illustrated, the HS features can include a HS signal portion 311, a HS component intensity 312, a cardiac timing interval (CTI) 313, or a CTI variability 314. The HS feature generator circuit can optionally include a signal transformation circuit 320. In an example, the HS features can include features ($F_{LV1}$) derived from the HS signal in response to a uni-site pacing of a first LV site ($LV_1$) capturing at least a portion of the heart (i.e., causes a depolarization that propagates throughout the LV chamber). The HS features can also include features ($F_{LV2}$) derived from the HS signal in response to a uni-site pacing of a different second LV site ($LV_2$) capturing at least a portion of the heart. The HS features can also include features ($F_{MSP}$) derived from the HS signal obtained during multi-site pacing of LV, such as pacing of the first and second LV sites ($LV_1$ and $LV_2$) within the same cardiac cycle, simultaneously or separated by a specified temporal offset less than a sensed or paced time interval value of the cardiac cycle. An example of the temporal offset is approximately between 0-100 msec.

The HS signal portion 311 can include a segment of the HS signal within a physiologic cycle, such as a cardiac cycle. The segment of the HS signal can include S1, S2, S3, or S4 component of the heart sound. The length of the segment can be approximately equal to or shorter than the size of detection window used for detecting respective HS component. For example, if an S1 window begins at 50 msec following an R wave and has duration of 300 msec, the HS signal portion 311 can be a "S1 segment" that includes the S1 component and has a duration up to 300 msec. In an example, the HS signal portion 311 can include a plurality of morphological feature points taken from the HS signal, such as data samples taken from the S1 segment. Examples of the morphological feature points can include characteristic samples including maximum, minimum, deflection point, among others.

The HS signal portion 311 can include an ensemble average of a segment of HS signal over multiple physiological cycles such as multiple cardiac cycles, or over a specified time period such as one minute, ten minutes, one hour, one day, etc. For example, an ensemble average can be taken over multiple S1 segments obtained from multiple cardiac cycles. The S1 segments can have identical duration and are aligned with respective to their respective fiducial points. Examples of the fiducial points can include Q wave or R wave of the same cardiac cycle, beginning point of S1 window, or a characteristic point of the detected S1 heart sound (e.g., peak of S1 segment), among others.

The HS component intensity 312 can include S1 intensity ($\|S1\|$), S2 intensity ($\|S2\|$), S3 intensity ($\|S3\|$), or S4 intensity ($\|S4\|$). Examples of the intensity HS component intensity can include amplitude of a detected HS component in a time-domain HS signal, a transformed HS signal such as integrated HS energy signal, or in a frequency-domain HS signal such as the peak value of the power spectral density. In some examples, the HS signal metrics generator circuit 331 can measure the HS intensity as the peak value of a generic measurement within the respective HS detection window, such as peak envelop signal or root-mean-squared value of the portion of the HS signal within the HS detection window.

The cardiac timing interval (CTI) 313 can indicate a timing interval between two cardiac events such as a cardiac electrical event detected from the cardiac electrical signal and a mechanical event such as detected from the HS signal or other physiologic signal indicative of cardiac mechanical or vibrational activity. The CTI can include a pre-ejection period (PEP), a systolic timing interval (STI), a diastolic timing interval (DTI), or a left ventricular ejection time (LVET), among others.

The PEP represents the total duration of the electrical and mechanical events prior to ejection. The PEP can include the electrical-mechanical delay which occurs between the onset of the ventricular depolarization and the beginning of ventricular contraction, and the isovolumetric contraction time during which the left ventricle can contract prior to the opening of the aortic valve. The PEP can be measured using one or more physiologic signals. In an example, the PEP can be measured as the time duration from the onset of the QRS to the S1 heart sound, i.e., PEP≈Q–S1 interval, or from the R wave to the S1 heart sound, i.e., PEP≈R–S1 interval. In another example, the PEP can be measured as the duration from the Q wave or the atrial activation event to the rise of the arterial pressure such as that measured from a carotid pulse wave. In an example, when no spontaneous QRS wave is present and the heart is electrically paced such as by using an IMD 110, the PEP can be measured from the ventricular pacing (Vp) signal to the beginning of ventricular ejection such as represented by the onset of S1 heart sound, that is, PEP≈Vp–S1 interval.

The STI represents the duration of total electro-mechanical systole. The STI spans from the electrical excitation of the heart to the closure of the aortic valve, and it contains two major components, namely the PEP and the LVET. The LVET represents the time interval from the opening to the closing of the aortic valve (mechanical systole). The STI can be measured using one or more physiologic signals sensed from physiologic sensors. Examples of the physiologic signals used for calculating STI or LVET include a heart sound signal, an intracardiac impedance signal, or a pressure signal. In an example, the STI can be measured as the interval from the onset of the QRS complex on the ECG or the atrial activation event in an intracardiac EGM to the S2 heart sound, that is, STI≈Q–S2 interval. In the case when the ventricle is paced (Vp), the STI can be measured from the ventricular pacing (Vp) signal to the end of ventricular ejection such as represented by the onset of S2 heart sound, that is, STI≈Vp–S2 interval.

The DTI represents the duration of total electro-mechanical diastole. The DTI spans from the closure of the aortic valve to the onset of the atrial depolarization in the next cardiac cycle. In an example, the DTI can be measured as the interval from the S2 heart sound to the onset of the QRS complex on the ECG or the atrial activation event in an intracardiac EGM of the next cardiac cycle, that is, DTI≈S2–Q interval. Therefore, a STI and the following DTI span the cardiac cycle, that is, cardiac cycle length (CL) =STI+DTI.

In some examples, the CTI can also include composite measures using two or more of the STI, the DTI, the PEP, the CL, or the LVET. Examples of the composite measures can include PEP/LVET ratio, STI/DTI ratio, STI/CL ratio, or DTI/CL ratio, among others.

The variability of cardiac timing interval (CTIvar) 314 can include variability of cardiac timing interval, such as the variability of STI, the variability of the DTI, the variability of the PEP, or the variability of LVET. The CTIvar can be indicative of the cardiac hemodynamics. The variability can be computed as a range, a variance, a standard deviation, a higher-order statistic, other measures of spreadness derived from a histogram or statistical distribution from multiple CTI measurements.

The signal transformation circuit 320 can be configured to compute a transformation of a HS signal or of the HS signal portion. In an example, the signal transformation circuit 320 can compute a transformation of a portion of HS signal during uni-site stimulation such as uni-site LV pacing, and a transformation of a portion of HS signal during multi-site stimulation such as multi-site LV pacing. The transformation can be a linear or a nonlinear transformation. The transformation $\Phi$ can be a causal or non-causal transformation. In an example, the transformation can include a dimensionality reduction transformation that transforms an N-dimensional signal feature vector to an M-dimensional (M<N) feature vector. The dimensionality reduction transformation can include a projection onto a subspace, or along a specified direction or a hyper-plane in a vector space. For example, a first S1 segment obtained from a HS signal in response to uni-site pacing of a first LV site ($LV_1$) can be represented by an N-dimensional morphological feature vector $F_{LV1}$ (e.g., N samples taken from the first S1 segment). Similarly, a second S1 segment obtained from a HS signal in response to uni-site pacing of a second LV site ($LV_2$) can be represented by an N-dimensional morphological feature vector $F_{LV2}$. The signal transformation circuit 320 can project the feature vectors $F_{LV1}$ and $F_{LV2}$ along a specified direction such as determined by linear discriminant analysis (LDA). When multiple S1 segments are respectively obtained during uni-site pacing at $LV_1$ and $LV_2$, the projection along the direction determined by LDA can maximize the separability in the vector space between the S1 segments obtained during different uni-site pacing. In another example, the signal transformation circuit can project the feature vectors $F_{LV1}$ and $F_{LV2}$ along a specified direction such as determined by principal component analysis (PCA). In another example, the signal transformation circuit 320 can project the feature vectors $F_{LV1}$ and $F_{LV2}$ along a specified direction such as determined by any other statistical method.

Figure 4:
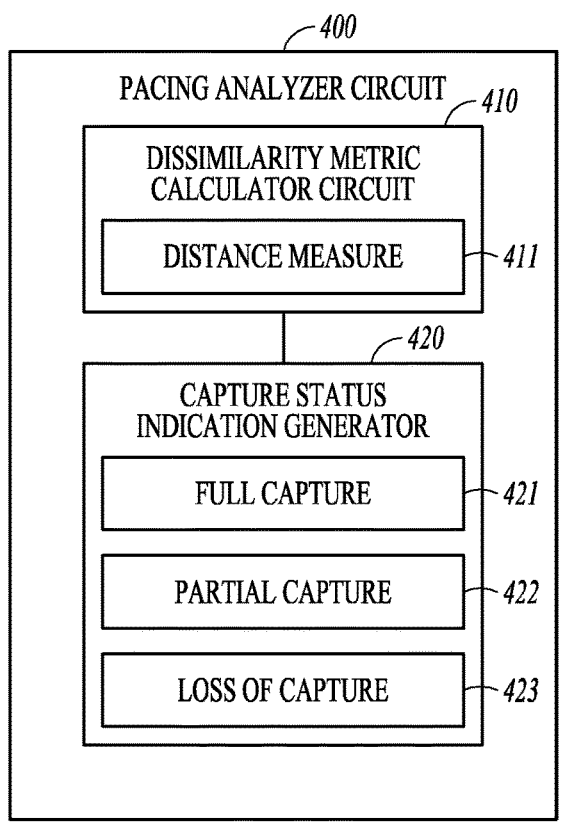
FIG. 4 illustrates an example of a pacing analyzer circuit.

FIG. 4 illustrates an example of a pacing analyzer circuit 400 configured to determine a capture status indication during multi-site stimulation. The pacing analyzer circuit 400 can be an embodiment of the pacing analyzer circuit 230, and includes a dissimilarity metric calculator circuit 410 and a capture status indication generator 420.

The dissimilarity metric calculator circuit 410 can be an embodiment of the comparator 231, and is configured to compute a dissimilarity metric between (1) the HS feature vector, $F_{LV1}$ or $F_{LV2}$, corresponding to uni-site stimulation such as uni-site LV pacing at $LV_1$ or $LV_2$, and (2) the HS feature vector $F_{MSP}$ corresponding to multi-site stimulation such as multi-site LV pacing at both $LV_1$ and $LV_2$ within the same cardiac cycle, simultaneously or separated by a specified temporal offset less than a sensed or paced time interval value of the cardiac cycle. The dissimilarity metric can include a distance measure 411 between $F_{MSP}$ and $F_{LV1}$, or between $F_{MSP}$ and $F_{LV2}$, denoted respectively by $d(F_{MSP}, F_{LV1})$ or $d(F_{MSP}, F_{LV2})$. Examples of the distance can include Euclidean distance, Mahalanobis distance, correlation coefficient, among other distance measures. In an example, the HS feature vectors ($F_{MSP}$, $F_{LV1}$, and $F_{LV2}$) each includes an ensemble average of a respective HS signal portion over multiple physiologic cycles. The dissimilarity metric calculator circuit 410 can calculate a distance between the ensemble average of the HS signal portion corresponding to uni-site LV pacing and the ensemble average of the HS signal portion corresponding to multi-site LV pacing. In another example, the HS feature vectors each includes a transformed HS signal portion. The dissimilarity metric calculator circuit 410 can calculate a distance between a transformation of the HS signal portion corresponding to uni-site LV pacing and a transformation of the HS signal portion corresponding to multi-site LV pacing. Examples of dissimilarity metric calculation are discussed below, such as with reference to FIGS. 5 and 6.

The capture status indication generator 420, as an embodiment of the capture status indication generator 232, can determine a capture status indication using the dissimilarity metric between $F_{MSP}$ and $F_{LV1}$, or between $F_{MSP}$ and $F_{LV2}$. The capture status indication indicates whether the multi-site stimulation, such as multi-site LV pacing at the first and second LV sites, captures at least a portion of the heart including the two or more sites. In an example, the distance $d(F_{MSP}, F_{LV1})$ or $d(F_{MSP}, F_{LV2})$ can each be compared against respective threshold to determine the capture status indication as one of a full capture indication, a partial capture indication, or a loss of capture indication. The full capture is achieved when the stimulation at the first and second stimulation sites each causes local capture, and results in depolarization that propagates throughout the LV chamber. The partial capture is achieved when only a part of the stimulation sites (such as only the first site or only the second site) causes capture. The loss of capture is resulted when none of the stimulation site causes capture. Examples of determining the capture status indication are discussed below, such as with reference to FIGS. 5 and 6.

Figure 5:
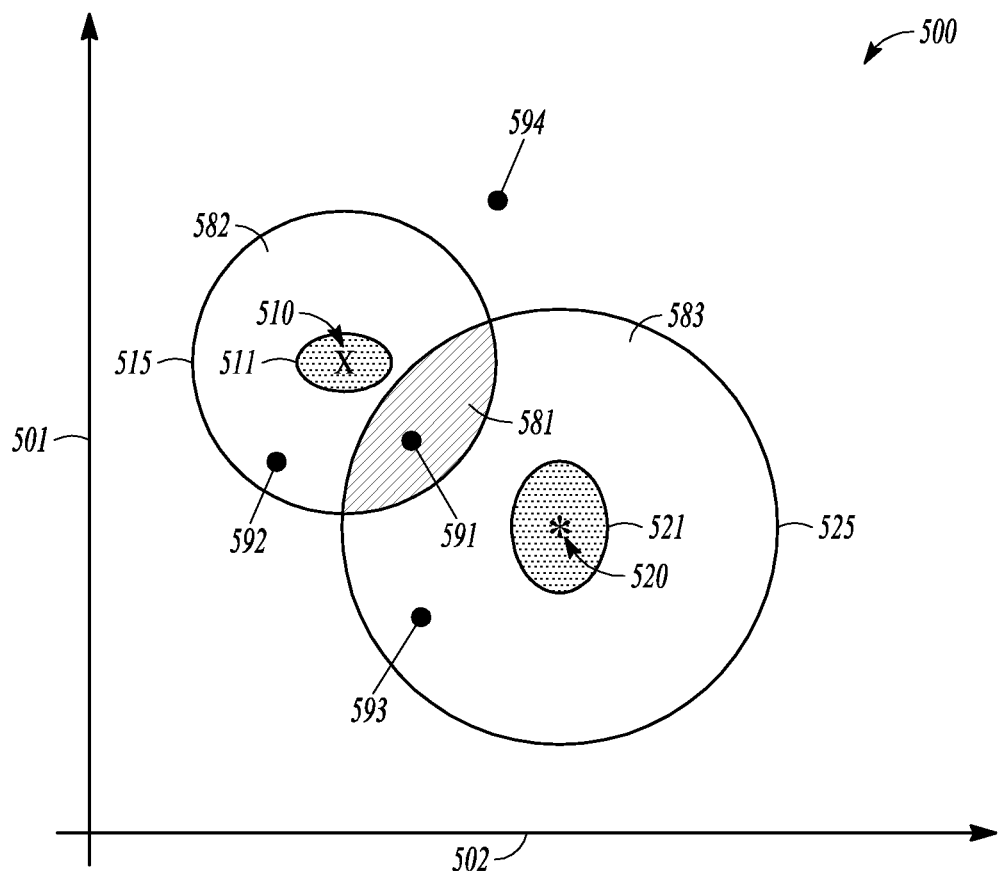
FIG. 5 illustrates an example of a diagram of determining capture status during multi-site stimulation of two LV sites $LV_1$ and $LV_2$.

FIG. 5 illustrates an example of a diagram 500 of determining capture status during multi-site stimulation such as pacing of two LV sites, $LV_1$ and $LV_2$, within the same cardiac cycle, simultaneously or separated by a specified temporal offset less than a sensed or paced time interval value of the cardiac cycle. An example of the temporal offset is approximately between 0-100 msec. A capture status indication can be determined based on a dissimilarity metric between a HS feature vector ($F_{MSP}$) corresponding to the multi-site stimulation and two HS feature vectors corresponding to two uni-site pacing. In the diagram 500, each HS feature vector can be represented as a point in an N-dimensional feature space, such as a two-dimensional feature space spanned by first feature 501 and second feature 502. In an example, a first set of HS feature vectors $\{F_{LV1}(i)\}$ can be obtained from a HS signal (such as S1 segment) over multiple physiologic cycles during uni-site pacing of the first LV site ($LV_1$), where the uni-site pacing of $LV_1$ captures at least a portion of the heart. The $\{F_{LV1}(i)\}$ have a statistical distribution represented by a mean HS feature vector 510 ($F_{LV1}$, such as computed as ensemble average of $\{F_{V1}(i)\}$) and a high-probable zone 511 defined by a covariance matrix of the first set of HS feature vectors $\{F_{LV1}(i)\}$. In an example, the first set of HS feature vectors $\{F_{LV1}(i)\}$ follows a normal distribution.

Similarly, a second set of HS feature vectors $\{F_{LV2}(j)\}$ can be obtained from a HS signal (such as S1 segment) over multiple physiologic cycles during uni-site pacing of a second LV site ($LV_2$), where the uni-site pacing of $LV_2$ captures at least a portion of the heart. The $\{F_{LV2}(j)\}$ have a statistical distribution represented by a mean HS feature vector 520 ($F_{LV2}$, such as computed as ensemble average of $\{F_{LV2\_}(j)\}$) and a high-probable zone 521 defined by a covariance matrix of the second set of HS feature vectors $\{F_{LV2}(j)\}$. In an example, the second set of HS feature vectors $\{F_{LV2}(j)\}$ follows a normal distribution.

The HS feature vector, $F_{MSP}$, corresponding to a multi-site stimulation such as LV pacing at both the first and second sites during the same cardiac cycle, can be represented by a point in the vector space, such as any of the points 591-594 as illustrated in FIG. 5. A first dissimilarity metric $M_1$ between $F_{MSP}$ and $F_{LV1}$ can be computed, such as a Euclidean distance in the feature space: $M_1 = d(F_{MSP}, F_{LV1}) = \|F_{MSP} - F_{LV1}\|$. Similarly, a second dissimilarity metric $M_2$ between $F_{MSP}$ and $F_{LV2}$ can be computed, such as a Euclidean distance in the feature spac0: $M_2 = d(F_{MSP}, F_{LV2}) = \|F_{MSP} - F_{LV2}\|$. In an example, Mahalanobis distance or other distance measures utilizing both the mean and the variance or covariance matrix of $\{F_{LV1}(i)\}$ or $\{F-_{LV12}(i)\}$ can be used in calculating the respective dissimilarity metrics $M_1$ or $M_2$.

The dissimilarity metrics $M_1$ and $M_2$ can be compared to respective first ($TH_1$) and second threshold ($TH_2$) to determine a classification of the capture status indication. A hypersphere in the N-dimensional vector space, such as a circle 515 centered at mean HS feature vector $F_{LV1}$ 510 with a radius of $TH_1$, defines a region such that any HS feature vectors inside the circle 515 is morphologically similar to the mean HS feature vector $F_{LV1}$ 510. Similarly, a hypersphere in the N-dimensional vector space, such as a circle 525 centered at mean HS feature vector $F_{LV2}$ 520 with a radius of $TH_2$, defines a region such that any HS feature vectors inside the circle 525 is morphologically similar to the mean HS feature vector $F_{LV2}$ 520.

In an example, if $F_{MSP}$ falls within a zone 581 defined by $M_1 \leq TH_1$ and $M_2 \leq TH_2$, then it indicates that $F_{MSP}$ is morphologically similar to both $F_{LV1}$ and $F_{LV2}$. This is an evidence of capture resulted from stimulation at both the first and second LV sites. As such, the capture status indication can be classified as a full capture. As an example, a HS feature vector 591 during multi-site LV pacing suggests that the stimulation at each site individually captures of the heart.

In an example, if $F_{MSP}$ falls within a zone 582 defined by $M_1 \leq TH_1$ and $M_2 > TH_2$, then it indicates that $F_{MSP}$ is morphologically similar to $F_{LV1}$ but not similar to $F_{LV2}$. This is an evidence of capture resulted from stimulation only at the first site, $LV_1$. As such, the capture status indication can be classified as a partial capture. As an example, a HS feature vector 592 during multi-site LV pacing suggests that only the stimulation at the first site, $LV_1$, captures of the heart, while the stimulation at the second site, $LV_2$, fails to capture the heart.

In an example, if $F_{MSP}$ falls within a zone 583 defined by $M_1 > TH_1$ and $M_2 \leq TH_2$, then it indicates that $F_{MSP}$ is morphologically similar to $F_{LV2}$ but not similar to $F_{LV1}$. This is an evidence of capture resulted from stimulation only at the second site, $LV_2$. As such, the capture status indication can be classified as a partial capture. As an example, a HS feature vector 593 during multi-site LV pacing suggests that only the stimulation at the second site, $LV_2$, captures of the heart, while the stimulation at the first site, $LV_1$, fails to capture the heart.

In another example, if $F_{MSP}$ falls outside a union of zones 581, 582 and 583, such that $M_1 > TH_1$ and $M_2 > TH_2$, then it indicates that $F_{MSP}$ is morphologically similar to neither $F_{LV1}$ nor $F_{LV2}$. This is an evidence of no capture produced by stimulation at either individual site. As such, the capture status indication can be classified as a loss of capture. As an example, a HS feature vector 594 during multi-site LV pacing suggests that the neither the stimulation at the first site $LV_1$, nor the stimulation at the second site $LV_2$, captures at least a portion of the heart.

Figure 6:
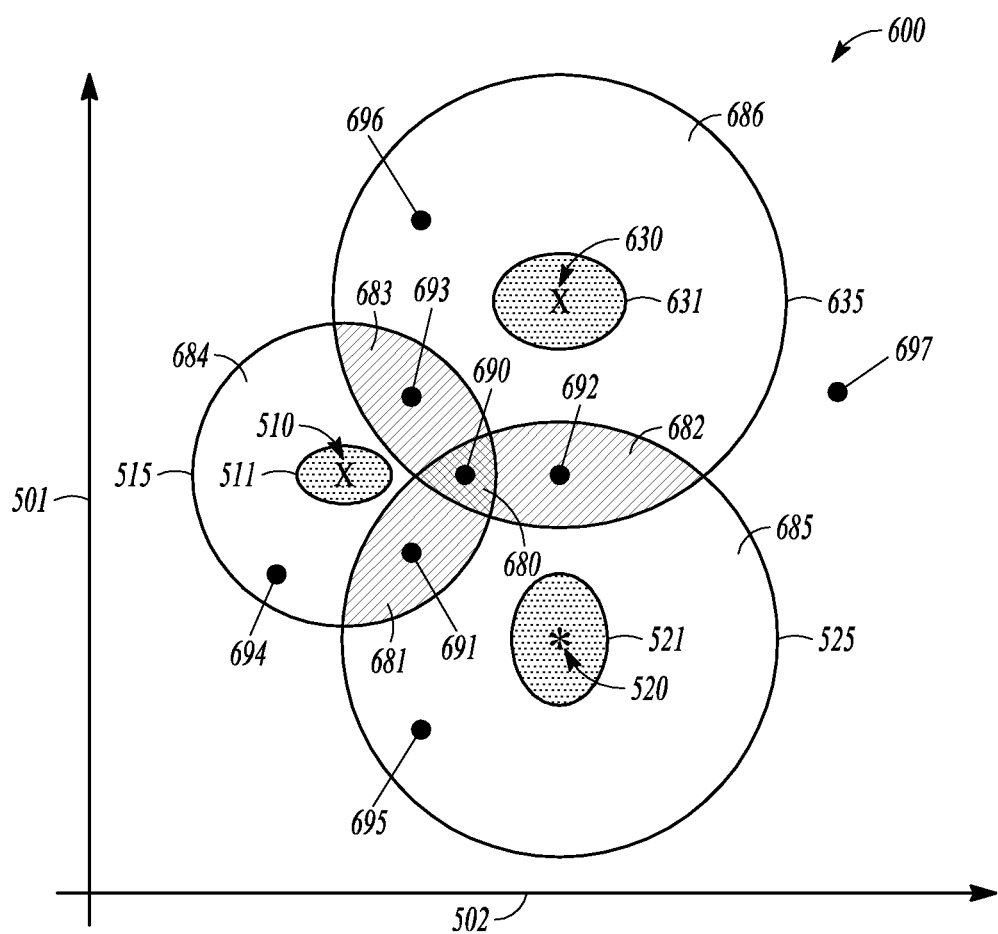
FIG. 6 illustrates an example of a diagram of determining capture status during multi-site stimulation of three LV sites $LV_1$, $LV_2$, and $LV_3$.

FIG. 6 illustrates an example of a diagram 600 of determining capture status during multi-site stimulation such as pacing of three LV sites, $LV_1$, $LV_2$, and $LV_3$, within the same cardiac cycle, simultaneously or separated by a specified temporal offset less than a sensed or paced time interval value of the cardiac cycle. A capture status indication can be determined based on dissimilarity metric between a HS feature vector corresponding to multi-site stimulation ($F_{MSP}$) and three HS feature vectors corresponding to three uni-site pacing. Similar to the diagram 500, the first set of HS feature vectors $\{F_{LV1}(i)\}$, corresponding to uni-site stimulation such as at the first LV site $LV_1$, can be represented by mean HS feature vector 510 ($F_{LV1}$) and a high-probable zone 511. The second set of HS feature vectors $\{F_{LV2}(j)\}$, corresponding to uni-site pacing at the second site $LV_2$, can be represented by mean HS feature vector 520 ($F_{LV2}$) and a high-probable zone 521. In addition, a third set of HS feature vectors $\{F_{LV3}(k)\}$, corresponding to uni-site pacing at a third site $LV_3$ different than the first and second LV sites, can be represented by mean HS feature vector 630 ($F_{LV3}$, such as computed as ensemble average of $\{F_{LV3}(k)\}$) and a high-probable zone 631. In an example, the third set of HS feature vectors $\{F_{LV3}(k)\}$ follows a normal distribution.

Similar to FIG. 5, dissimilarity metrics, such as Euclidean distances, can be computed between $F_{MSP}$ and one of the $F_{LV1}$, $F_{LV2}$, or $F_{LV3}$: $M_1 = \|F_{MSP} - F_{LV1}\|$, $M_2 = \|F_{MSP} - F_{LV2}\|$, and $M_3 = \|F_{MSP} - F_{LV3}\|$. In an example, Mahalanobis distance or other distance measures utilizing both the mean and the variance or covariance matrix can be used to calculate the respective similarity metrics $M_1$, $M_2$, or $M_3$.

The dissimilarity metrics $M_1$, $M_2$ or $M_3$ can be compared to their respective thresholds $TH_1$, $TH_2$, or $TH_3$ to determine a classification of the capture status indication. Similar to circles 515 and 525, a circle 635 centered at the mean HS feature vector $F_{LV3}$ 630 with a radius of $TH_3$ defines a region such that any HS feature vectors inside the circle 635 is morphologically similar to the mean HS feature vector $F_{LV3}$ 630. In an example, if $F_{MSP}$ falls within a zone 680 defined by $M_1 \leq TH_1$, $M_2 \leq TH_2$, and $M_3 \leq TH_3$, then it indicates that $F_{MSP}$ is morphologically similar to all three HS feature vectors $F_{LV1}$, $F_{LV2}$, and $F_{LV3}$. This is an evidence of capture resulted from stimulation at all three LV sites. As such, the capture status indication can be classified as a full capture. As an example, a HS feature vector 690 during multi-site LV pacing suggests that the stimulation at each of the three sites individually captures of the heart.

In an example, if $F_{MSP}$ falls within a zone 681 defined by $M_1 \leq TH_1$, $M_2 \leq TH_2$, and $M_3 > TH_3$, then it indicates that $F_{MSP}$ is morphologically similar to $F_{LV1}$ and $F_{LV2}$ but not similar to $F_{LV3}$. The capture status indication can then be classified as a partial capture, where the capture results from stimulation only at $LV_1$ and $LV_2$, not at $LV_3$. The HS feature vector 691 during multi-site LV pacing is an example of such partial capture. In another example, if $F_{MSP}$ falls within a zone 682 defined by $M_2 \leq TH_2$, $M_3 \leq TH_3$, and $M_1 > TH_1$, then it indicates that $F_{MSP}$ is morphologically similar to $F_{LV2}$ and $F_{LV3}$ but not similar to $F_{LV1}$. The capture status indication can then be classified as a partial capture where the capture results from stimulation only at $LV_2$ and $LV_3$, not at $LV_1$. The HS feature vector 692 during multi-site LV pacing is an example of such partial capture. In an example, if $F_{MSP}$ falls within a zone 683 defined by $M_1 \leq TH_1$, $M_3 \leq TH_3$, and $M_2 > TH_2$, then it indicates that $F_{MSP}$ is morphologically similar to $F_{LV1}$ and $F_{LV3}$ but not similar to $F_{LV2}$. The capture status indication can then be classified as a partial capture where the capture results from stimulation at only $LV_1$ and $LV_3$, not at $LV_2$. The HS feature vector 693 during multi-site LV pacing is an example of such partial capture.

In an example, if $F_{MSP}$ falls within a zone 684 defined by $M_1 \leq TH_1$, $M_2 > TH_2$, and $M_3 > TH_3$, then it indicates that $F_{MSP}$ is morphologically similar to $F_{LV1}$, but not similar to $F_{LV2}$ or $F_{LV3}$. The capture status indication can then be classified as a partial capture where the capture results from stimulation at only the site $LV_1$. The HS feature vector 694 during multi-site LV pacing is an example of such partial capture. In an example, if $F_{MSP}$ falls within a zone 685 defined by $M_2 \leq TH_2$, $M_3 > TH_3$, and $M_1 > TH_1$, then it indicates that $F_{MSP}$ is morphologically similar to $F_{LV2}$ but not similar to $F_{LV1}$ or $F_{LV3}$. The capture status indication can then be classified as a partial capture where the capture results from stimulation at only $LV_2$. The HS feature vector 695 during multi-site LV pacing is an example of such partial capture. In another example, if $F_{MSP}$ falls within a zone 686 defined by $M_3 \leq TH_3$, $M_1 > TH_1$, and $M_2 > TH_2$, then it indicates that $F_{MSP}$ is morphologically similar to $F_{LV3}$ but not similar to $F_{LV1}$ or $F_{LV2}$. The capture status indication can be classified as a partial capture where the capture results from stimulation only at $LV_3$. The HS feature vector 696 during multi-site LV pacing is an example of such partial capture.

In an example, if $F_{MSP}$ falls outside a union of zones 680, 681, 682, 683, 684, 685 and 686, such that $M_1 > TH_1$, $M_2 > TH_2$, and $M_3 > TH_3$, then it indicates that $F_{MSP}$ is morphologically similar to none of $F_{LV1}$, $F_{LV2}$, or $F_{LV3}$. This is an evidence of no capture resulted from stimulation at any individual site. As such, the capture status indication can be classified as a loss of capture. As an example, a HS feature vector 697 during multi-site LV pacing suggests that none of the three individual sites captures at least a portion of the heart.

Figure 7:
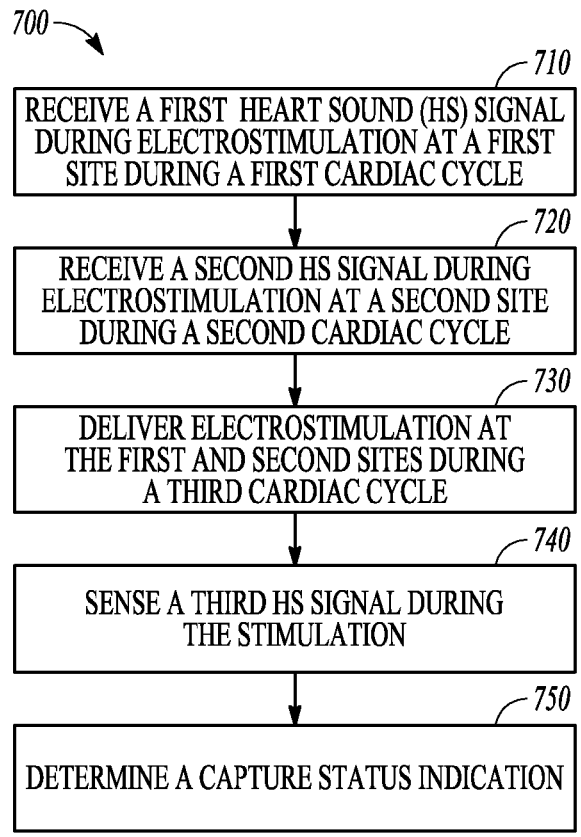
FIG. 7 illustrates an example of a method for evaluating electrostimulation of a heart of a subject.

FIG. 7 illustrates an example of a method 700 for evaluating electrostimulation of a heart of a subject. The method 700 can be implemented and operate in an implantable, wearable, or other ambulatory medical device, or in a remote patient management system. In an example, the method 700 can be performed by the heart sound based multi-site pacing capture verification circuit 200 or any modification thereof.

The method 700 can begin at step 710, where a first heart sound (HS) signal can be received during electrostimulation at a first site of the heart at a first cardiac cycle. The electrostimulation can be produced such as by the IMD 100 and delivered to the two or more sites of the heart via the lead system 108A-C and the electrodes on the respective leads. The first site can include an anatomical region inside, or on an epicardial surface of, one or more heart chambers including RA, RV, LA, and LV, or the tissues between the chambers. In an example, the first site can include a site at a left ventricle (LV) of the heart, and the electrostimulation at the LV site can include unipolar or bipolar stimulation such as via one or more electrodes positioned on a portion of the LV such as epicardial surface of the LV. The first HS signal can be obtained such as by using a HS sensor capable of sensing physiologic information indicative of mechanical or vibrational activities of the heart. Examples of the HS sensor can include accelerometer, microphone, piezo-based sensor, or other vibrational or acoustic sensors. The HS sensor can sense the first HS signal when the electrostimulation at the first site captures at least a portion of the heart. For example, the stimulation at the first LV site $LV_1$ causes depolarization that propagates throughout the LV chamber. Alternatively or additionally, the first HS signal can be received from a device capable of collecting or storing the HS information, such as an external programmer, an electronic medical record system, a memory unit, or other data storage devices.

At 720, a second HS signal can be received during electrostimulation at a second site of the heart different from the first site during a second cardiac cycle. In an example, the second HS signal can be sensed from a HS sensor or received from a storage device when the electrostimulation at the second site captures at least a portion of the heart. In an example, the first and second stimulation sites are located at different heart chambers. In another example, the second site can be located at the same heart chamber as the first stimulation site, such as the LV of the heart. In an example, electrostimulation at the first and second sites include unipolar or bipolar pacing using different electrodes on the LV lead 133.

At 730, multi-site electrostimulation can be delivered to the heart, such as pacing of the first and second sites of the heart within the same cardiac cycle, simultaneously or separated by a specified temporal offset less than a sensed or paced time interval value of the cardiac cycle. In an example, a multi-site LV pacing using two or more LV pacing vectors can be performed at 730. Each LV pacing vector involves an anode and a cathode. One or both of the anode and the cathode can be selected from the two or more electrodes removably positioned inside or on the epicardial surface of the LV. In an example, the multi-site LV pacing can be delivered using one or more of a bipolar pacing between two LV electrodes, a bipolar pacing between an LV electrode and a RV or RA electrode, or a unipolar pacing between an LV electrode and the IMD can 112.

At 740, a third HS signal can be sensed during the multi-site electrostimulation, such as by using a HS sensor. The first, second, and third HS signals can each be processed, including amplification, digitization, filtering, or other signal conditioning operations. The processed HS signal can further be analyzed such as detecting one or more HS components including S1, S2, S3 or S4 heart sounds. In an example, the HS components can be detected using respective time windows applied to the HS signal. Signal characteristics, such as peaks of the signal amplitude or signal power, can be detected from the HS signal within the respective time windows.

At 750, a capture status indication can be determined using the third HS signal obtained during the multi-site electrostimulation, and at least one of the first or second HS signal obtained during the uni-site electrostimulation that captures at least a portion of the heart. In an example, the first, second, and the third HS signal can be processed to compute respective HS feature vectors. The capture status indication can be determined based on a comparison between the HS features of the third HS signal and the HS features of at least one of the first or second HS signal. The capture status indication can indicate whether the electrostimulation at all the stimulation sites capture the cardiac tissue, or only the electrostimulation at a part of the stimulation sites capture the cardiac tissue. Examples of the capture status indication based on the HS features are discussed below, such as with reference to FIG. 8.

Figure 8:
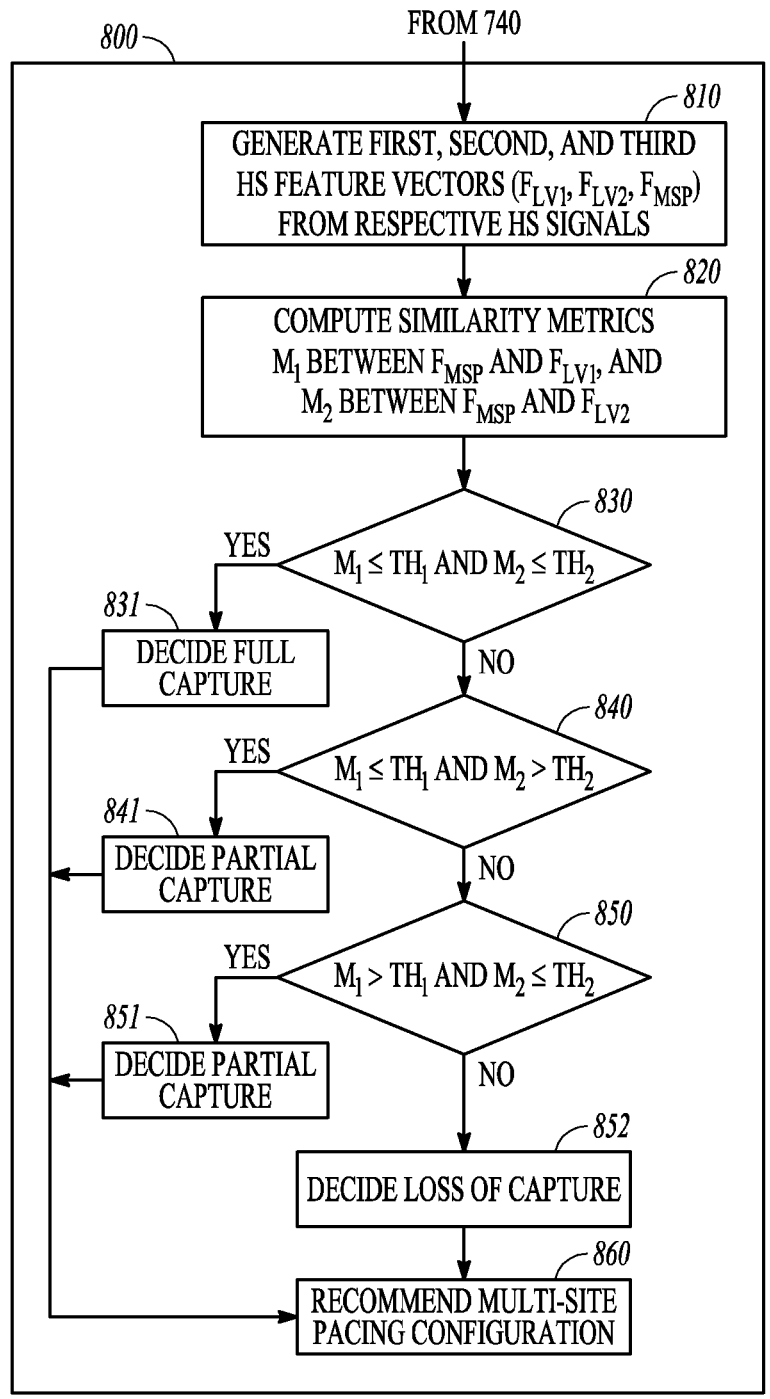
FIG. 8 illustrates an example of a method for determining capture status indication.

FIG. 8 illustrates an example of a method 800 for determining capture status indication, which can be an embodiment of capture status indication at step 750. The method 800 begins at step 810, where first, second, and third HS feature vectors ($F_{LV1}$, $F_{LV2}$, $F_{MSP}$) can be generated from the respective first, second, and third HS signals. In an example, the HS feature vector can include a HS signal portion, such as a segment of the HS signal within a physiologic cycle such as a cardiac cycle. The segment of the HS signal can include S1, S2, S3, or S4 component of the heart sound. The length of the segment can be approximately equal to or shorter than the size of detection window used for detecting respective HS component.

In an example, the HS feature vector can include a plurality of morphological feature points, such as data samples taken from a portion of the HS. In an example, the HS signal portion can include an ensemble average of a segment of HS signal over multiple physiological cycles such as multiple cardiac cycles, or over a specified time period such as one minute, ten minutes, one hour, one day, etc. For example, the ensemble average can be taken over multiple S1 segments obtained from multiple cardiac cycles.

The HS feature vectors can include other morphological features or statistical features. In an example, the HS feature vector can include intensity of a HS component, such as S1 intensity (∥S1∥), S2 intensity (∥S2∥), S3 intensity (∥S3∥), or S4 intensity (∥S4∥). Examples of the intensity can include amplitude of a detected HS component in a time-domain HS signal, a transformed HS signal such as integrated HS energy signal, or in a frequency-domain HS signal such as the peak value of the power spectral density. In another example, the HS feature vector can include a cardiac timing interval (CTI), such as pre-ejection period (PEP), a systolic timing interval (STI), a diastolic timing interval (DTI), or a left ventricular ejection time (LVET), among others. The CTI can be measured as time intervals between two cardiac events such as a cardiac electrical event detected from the cardiac electrical signal and a mechanical event such as detected from the HS signal or other physiologic signal indicative of cardiac mechanical or vibrational activity. In yet another example, the HS feature vector can include a variability of CTI (CTIvar), such as the variability of STI, the variability of the DTI, the variability of the PEP, or the variability of LVET. The CTIvar can be indicative of the cardiac hemodynamics. The variability can be computed as a range, a variance, a standard deviation, a higher-order statistic, other measures of spreadness derived from a histogram or statistical distribution from multiple CTI measurements.

In some examples, the HS feature vectors can include a transformation of a HS signal or a transformation of the HS signal portion. The transformation can include linear or nonlinear transformation. In an example, the transformation includes a dimensionality reduction transformation that transforms an N-dimensional signal feature vector to an M-dimensional (M<N) feature vector. For example, an N-dimensional HS feature vector (such as the S1 segment containing N samples) can be projected onto a subspace, such as along a specified direction, in a vector space. In an example, the specified direction can be determined by linear discriminant analysis (LDA). The direction of projection determined by LDA can maximizes the separability between a plurality of HS feature vectors obtained from the first HS signal over multiple cardiac cycles, and a plurality of HS feature vectors obtained from the second HS signal over multiple cardiac cycles. In another example, the specified direction can be determined by principal component analysis (PCA), or by any other statistical method.

At 820, a first dissimilarity metric $M_1$ can be computed between the HS feature vectors $F_{MSP}$ and $F_{LV1}$, and a second dissimilarity metric $M_2$ can be computed between the HS feature vectors $F_{MSP}$ and $F_{LV2}$. In an example, the HS feature vector $F_{LV1}$ or $F_{LV2}$ can be generated from an ensemble average of respective HS signals over multiple physiologic cycles. The similarity metric can include a Euclidean distance between $F_{MSP}$ and $F_{LV1}$ or an Euclidean distance between $F_{MSP}$ and $F_{LV2}$, i.e., $M_1=d(F_{MSP}, F_{LV1})=\|F_{MSP}-F_{LV1}\|$ and $M_2=d(F_{MSP}, F_{LV2})=\|F_{MSP}-F_{LV2}\|$. In some examples, the similarity metric can include a Mahalanobis distance which utilizes both the ensemble average (i.e., the mean) and the variance or covariance matrix of the respective HS feature vector to calculate the distance.

At 830, the dissimilarity metrics $M_1$ and $M_2$ can be compared to respective first ($TH_1$) and second threshold ($TH_2$) to determine a classification of the capture status indication. If $M_1 \leq TH_1$ and $M_2 \leq TH_2$, then it indicates that the HS feature vector corresponding to multi-site pacing, $F_{MSP}$, is morphologically similar to both the HS feature vectors during uni-site pacing at respective LV sites, $F_{LV1}$ and $F_{LV2}$. This is an evidence of capture resulted from stimulation at both the first and second LV sites. As such, at 831 the capture status indication can be classified as a full capture, which indicates that the stimulation at the first ($LV_1$) and second stimulation sites ($LV_2$) each causes local capture, and results in depolarization that propagates throughout the LV chamber.

If the condition at 830 is not satisfied, but at 840 the $F_{MSP}$ falls within a region such that $M_1 \leq TH_1$ and $M_2 > TH_2$, then it indicates that $F_{MSP}$ is morphologically similar to $F_{LV1}$ but not similar to $F_{LV2}$. This is an evidence of capture resulted from stimulation only at the first site, $LV_1$, while the stimulation at the second site, $LV_2$, fails to capture the heart. As such, the capture status indication can be classified as a partial capture at 841.

If the condition at 840 is not satisfied, but at 850 the $F_{MSP}$ falls within a region such that $M_1 > TH_1$ and $M_2 \leq TH_2$, then it indicates that $F_{MSP}$ is morphologically similar to $F_{LV2}$ but not similar to $F_{LV1}$. This is an evidence of capture resulted from stimulation at only the second site, $LV_2$, while the stimulation at the first site, $LV_1$, fails to capture the heart. As such, the capture status indication can be classified as a partial capture at 851. However, if the condition at 850 is not satisfied, i.e., the $F_{MSP}$ falls within a region such that $M_1 > TH_1$ and $M_2 > TH_2$, then it indicates that $F_{MSP}$ is morphologically similar to neither $F_{LV1}$ nor $F_{LV2}$. This is an evidence of no capture resulted from stimulation at either site. As such, the capture status indication can be classified as a loss of capture at 852.

The capture status indications, including the full capture decision at 831, the partial capture decisions at 841 or 851, and the loss of capture decision at 852, can be presented to a system user such as a clinician. A recommendation of multi-site pacing configuration can be generated at 860, such as by displaying capture status indication and the recommended pacing configuration in a user interface. In an example, in response to the decision of full capture indication, the existing multi-site pacing configuration can be confirmed and recommended for subsequent therapy. Alternatively, one or more parameters associated with the delivery of multi-site stimulation can be adjusted such as automatically by a therapy control circuit. For example, amplitude, pulse width of stimulation pulse, duty cycles, frequency, or other intensity parameters of multi-site stimulation can be reduced to lower the energy consumption while maintaining effective full capture at both the first and second stimulation sites. In another example, in response to the decision of partial capture indication, electrostimulation of at least one of the stimulation sites can be adjusted, such as the site that fails to elicit capture (e.g., site $LV_2$ due to the partial capture decision at 841, or site $LV_1$ due to the partial capture decision at 851). The adjustment of stimulation configuration can include selecting an alternative stimulation site (such as by repositioning the stimulation electrode), increasing the stimulation intensity or frequency, alternating the pacing vector (e.g., switching from a unipolar stimulation to bipolar stimulation), or alternating the polarity of the stimulation. In another example, in response to the decision of loss of capture indication, electrostimulation of at both the first and second stimulation sites (such as $LV_1$ and $LV_2$) can be adjusted, such as by repositioning the stimulation electrodes or changing the stimulation energy or configurations so as to achieve desired capture status. In an example, therapy such as multi-site stimulation can then be delivered based at least in part on the capture status indication.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B"

includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for evaluating electrostimulation of a heart, comprising:
   an electrostimulation circuit, configured to deliver multi-site electrostimulation to two or more sites of a chamber of the heart;
   a heart sound (HS) sensor circuit, configured to sense a HS signal during the multi-site electrostimulation delivered to the two or more sites; and
   a pacing analyzer circuit, in communication with the HS sensor circuit, configured to determine a capture status indication associated with the multi-site electrostimulation using a comparison of a morphology of the HS signal sensed during the multi-site electrostimulation to HS morphologies corresponding to electrostimulation at each of the two or more sites of the heart,
   wherein the capture status indication includes one or more of a full capture indication indicating the multi-site electrostimulation captures each of the two or more sites, or a partial capture indication indicating the multi-site electrostimulation captures at least one of the two or more sites and fails to capture at least another one of the two or more sites.

2. The system of claim 1, wherein:
   the HS sensor circuit is configured to sense a first HS signal corresponding to electrostimulation at a first site of the chamber of the heart, to sense a second HS signal corresponding to electrostimulation at a second site of the chamber of the heart, and to sense a third HS signal corresponding to the multi-site electrostimulation at both the first and second sites; and
   the pacing analyzer circuit is configured to determine the capture status indication using a comparison between the morphology of the third HS signal and each of the morphologies of the first and second HS signals, the capture status indication indicative of whether the multi-site electrostimulation captures both the first and second sites;
   wherein the capture status indication indicates a full capture when the multi-site electrostimulation captures both the first and the second sites, or a partial capture when the multi-site electrostimulation captures only one of the first or the second site.

3. The system of claim 2, wherein the pacing analyzer circuit is configured to:
   generate a third HS feature vector using the third HS signal, and first and second HS feature vectors using respectively the first or second HS signal, the first, second, or third feature vector each including a respective morphological feature;
   compute a first dissimilarity metric between the third HS feature vector and the first feature vector, and a second dissimilarity metric between the third HS feature vector and the second HS feature vector; and
   determine the capture status indication in response to the first and second dissimilarity metrics satisfying respective conditions.

4. The system of claim 3, wherein the pacing analyzer circuit is configured to:
   receive a first threshold value and a second threshold value; and
   determine a full capture indication in response to the first dissimilarity metric falling below the first threshold value and the second dissimilarity metric falling below the second threshold value, or a partial capture indication in response to only one of the first or second dissimilarity metric falling below the respective first or second threshold value.

5. The system of claim 3, wherein the third HS feature vector includes a portion of the third HS signal including a specified HS component, and the first or second HS feature vector includes respectively a portion of the first or second HS signal including the specified HS component, wherein the specified HS component includes one of S1, S2, S3 or S4 heart sound components.

6. The system of claim 3, wherein the third HS feature vector further includes an intensity parameter of the third HS signal, and the first or second HS feature vector further includes respectively an intensity parameter of the first or second HS signal, wherein the intensity parameter includes amplitude of one of S1, S2, S3 or S4 heart sound components.

7. The system of claim 3, wherein the third HS feature vector further includes a cardiac timing interval (CTI) parameter computed using the third HS signal, and the first or second HS feature vector further includes respectively the CTI parameter computed using the first or second HS signal, wherein the CTI parameter includes one or more of a systolic time interval, a pre-ejection interval, a diastolic interval, or a left ventricle ejection time.

8. The system of claim 3, wherein the first dissimilarity metric includes a distance between the third HS feature vector and the first HS feature vector in a vector space, and the second dissimilarity metric includes a distance between the third HS feature vector and the second HS feature vector in the vector space.

9. The system of claim 3, wherein the pacing analyzer circuit is configured to:
 compute an ensemble average of a portion of the third HS signal over multiple physiological cycles, an ensemble average of a portion of the first HS signal over multiple physiological cycles, and an ensemble average of a portion of the second HS signal over multiple physiological cycles;
 compute the first dissimilarity metric including a distance between the ensemble average of the portion of the third HS signal and the ensemble average of the portion of the first HS signal; and
 compute the second dissimilarity metric including a distance between the ensemble average of the portion of the third HS signal and the ensemble average of the portion of the second HS signal.

10. The system of claim 3, wherein the pacing analyzer circuit is configured to:
 transform a portion of third HS signal, a portion of the first HS signal, and a portion of the second HS signal;
 compute the first dissimilarity metric including a distance between the transformed portion of third HS signal and the transformed portion of the first HS signal; and
 compute the second dissimilarity metric including a distance between the transformed portion of third HS signal and the transformed portion of the second HS signal.

11. The system of claim 10, wherein the transformation of the portion of the third HS signal, the portion of the first HS signal, and the portion of the second HS signal includes a projection of each of the portion of the third HS signal, the portion of the first HS signal, and the portion of the second HS signal onto a subspace or a specified direction in a vector space.

12. The system of claim 1, further comprising a therapy controller circuit coupled to the electrostimulation circuit, the therapy controller circuit configured to determine at least one therapy parameter based on the capture status indication, wherein the electrostimulation circuit is configured to deliver the electrostimulation according to the determined therapy parameter.

13. The system of claim 1, wherein the HS sensor circuit is coupled to an accelerometer or a microphone configured to detect the HS signal including mechanical or acoustic activity of the heart indicative of HS.

14. The system of claim 1, wherein the electrostimulation circuit is configured to deliver the multi-site electrostimulation to two or more sites of the left ventricle (LV) during a cardiac cycle, simultaneously or separated by a specified temporal offset less than a sensed or paced interval value of the cardiac cycle.

15. A method for evaluating electrostimulation of a heart, comprising:
 receiving a first heart sound (HS) morphology corresponding to electrostimulation at a first site of a chamber of the heart, and a second HS morphology corresponding to electrostimulation at a different second site of the chamber of the heart;
 delivering multi-site electrostimulation to two or more sites including both the first and second sites of the chamber of the heart;
 sensing a third HS signal during the delivery of the multi-site electrostimulation; and
 determining a capture status indication associated with the multi-site electrostimulation using a comparison of a morphology of the third HS signal to the received first and second HS morphologies, wherein the capture status indication includes one or more of a full capture indication indicating that the multi-site electrostimulation captures each of the two or more sites, or a partial capture indication indicating that the multi-site electrostimulation captures at least one of the two or more sites and fails to capture at least another one of the two or more sites.

16. The method of claim 15, wherein receiving the first and second HS morphologies includes receiving first and second HS signals during stimulation of respective first and second sites of a left ventricle (LV) of the heart, wherein the capture status indication indicates a full capture when the multi-site electrostimulation captures both the first and the second sites, or a partial capture when the multi-site electrostimulation captures only one of the first or the second site.

17. The method of claim 16, further comprising generating a third HS feature vector using the third HS signal, generating a first HS feature vector using the first HS signal, and generating a second HS feature vector using the second HS signal, the first, second, or third feature vector each including a respective morphological feature;
 computing a first dissimilarity metric between the third HS feature vector and the first feature vector, and a second dissimilarity metric between the third HS feature vector and the second feature vector; and
 determining the capture status indication in response to the first and second dissimilarity metrics satisfying respective conditions.

18. The method of claim 17, further comprising:
 receiving a first threshold value and a second threshold value, wherein:
 determining the capture status indication includes determining a full capture indication in response to the first dissimilarity metric falling below the first threshold value and the second dissimilarity metric falling below the second threshold value, or a partial capture indication in response to only one of the first or second dissimilarity metric falling below the respective first or second threshold value.

19. The method of claim 17, wherein the first dissimilarity metric includes a distance between the third HS feature vector and the first HS feature vector in a vector space, and the second dissimilarity metric includes a distance between the third HS feature vector and the second HS feature vector in the vector space.

20. The method of claim 17, wherein the first, second, or third HS feature vector each further includes one or more of a signal portion, a transformed signal portion including a projection of a signal portion, an intensity measure, or a cardiac timing interval parameter of the respective HS signals.

\* \* \* \* \*